United States Patent [19]

Ehrenpreis et al.

[11] Patent Number: 4,579,843

[45] Date of Patent: Apr. 1, 1986

[54] ANALGESIC AND ANTI-INFLAMMATORY COMPOSITIONS

[75] Inventors: Seymour Ehrenpreis, Skokie; Joseph E. Comaty, DesPlaines; Reuben C. Balagot, Chicago, all of Ill.

[73] Assignee: Endorfin, Inc., Chicago, Ill.

[21] Appl. No.: 657,681

[22] Filed: Oct. 4, 1984

Related U.S. Application Data

[60] Continuation-in-part of Ser. No. 394,698, Jul. 2, 1982, abandoned, which is a division of Ser. No. 75,663, Sep. 14, 1979, Pat. No. 4,439,452, which is a continuation-in-part of Ser. No. 12,043, Feb. 14, 1979, abandoned, which is a continuation-in-part of Ser. No. 882,975, Mar. 3, 1978, abandoned.

[51] Int. Cl.$^4$ .......................................... A61K 31/615
[52] U.S. Cl. .................................................. 514/162
[58] Field of Search ........................................ 514/162

[56] References Cited

PUBLICATIONS

Hughes, Brain Research, 88 (1975), pp. 295–308.
Paul D. Boyer, The Enzymes, vol. III, 3rd Ed., pp. 9–11, 50–56, Academic Press, New York & London (1971).
Cox et al., Proc. Natl. Acad. Sci. USA, 73 (1976) pp. 1821–1823.
Lazarus et al., Proc. Natl. Acad. Sci. USA, 73, 1976, pp. 2156–2159.
Ling et al., Chem. Abst., 86 (1977) p. 38887h.
Ling et al., Proc. Natl. Acad. Sci. USA, 73 (1976) pp. 3308–3310.
Guillemin et al., Biochemie (1976), pp. 783–785.
Bradbury et al., Nature, 260, (1976) pp. 793–795.
Li et al., Proc. Natl. Acad. Sci. USA (1976) pp. 1145–1148.
Coy et al., Biochem & Biophys. Res. Comm., 73, 1976, pp. 632–638.
Markes et al., Biochem & Biophys. Res. Comm., 74 (1977) pp. 1552–1559.
Ling et al., Biochem & Biophys. Res. Comm., 74 (1977), pp. 248–255.
Pert et al., Science, 194, 330–332, (1976).
Kosterlitz et al., Life Sciences, 17, pp. 91–96 (1975).
Plotnikoff et al., Life Sciences, 19, pp. 1283–1288 (1976).
Pert et al, Opiates & Endogenous Opiate Peptides, (1976), pp. 79–86.

Primary Examiner—Stanley J. Friedman
Attorney, Agent, or Firm—Niblack & Niblack

[57] ABSTRACT

Analgesic and anti-inflammatory compositions are provided which comprise a therapeutically effective amount of a first agent selected from the group consisting of D-phenylalanine, DL-phenylalnine, D-leucine, and DL-leucine and synergistically effective amount of a second therapeutic agent selected from the group consisting of aspirin and an aspirin-type non-steroidal anti-inflammatory, anti-pyretic agent.

18 Claims, No Drawings

ANALGESIC AND ANTI-INFLAMMATORY COMPOSITIONS

CROSS-REFERENCE TO RELATED APPLICATIONS

This application is a continuation-in-part of copending application Ser. No. 394,698, filed July 2, 1982, which is a divisional application under Rule 60 of application Ser. No. 75,663 filed Sept. 14, 1979, issued Mar. 27, 1984, U.S. Pat. No. 4,439,452, which was a continuation-in-part of application Ser. No. 12,043, filed Feb. 14, 1979, now abandoned, which in turn was a continuation-in-part of Ser. No. 882, 975, filed Mar. 3, 1978, all are now abandoned.

FIELD OF THE INVENTION

This invention relates to analgesia, and/or inflammation, and more particularly relates to pharmaceutical compositions employed in treating pain and/or inflammation and which comprise a combination of a first therapeutic agent selected from the group consisting of D-phenylalanine, DL-phenylalanine, D-leucine, DL-leucine and hydrocinnamic acid and a second therapeutic agent selected from the group consisting of aspirin and a non-steroidal, aspirin like anti-inflammatory, antipyretic agent.

BACKGROUND OF THE INVENTION

Enkephalins and endorphins are morphine-like substances which have recently been discovered to be endogenous in various animal species, including mammals and man, and serve as the body's natural pain relievers. Enkephalins and endorphins are peptides and/or polypeptides. Enkephalins are normally present in the brain.

It has heretofore been observed that enkephalins and endorphins have an ability to act as analgesics to abolish pain when administered to various animals by certain special routes (e.g. directly into the brain) which pose practical drawbacks to useful administration. Further, these substances have a serious drawback in that they are addicting, and tolerance develops to them. In addition, they have an effect of very short duration of action when administered to mammalian hosts, due to their rapid destruction by other substances endogenous to animal species, including mammals and man. These endogenous substances that destroy the action of enkephalins were originally believed to include at least two known enzymes, carboxypeptidase A and leucine aminopeptidase. It was since learned, however, that carboxypeptidase A is not involved in the destruction of the enkephalins and endorphins.

Regardless of the endogenous substances responsible for the destruction of enkephalin when isolated or synthesized and administered to mammals, in an attempt to overcome the problem, various derivatives of enkephalin, the endorphins and other beta-lipotropin fragments 61–91 were synthesized, and reported in the literature. Based on earlier successful attempts by Coy and Schally to block enzymatic degradation upon administration of LHRH leutinizing hormone by replacing a naturally occuring amino acid in the naturally occuring peptide sequence with a D-amino acid, D-alanine, and other D-amino acids including D-leucine and D-phenlylanine, were introduced into the amino acid sequence of enkephalin and other beta-lipotropin fragments 61–91 in place of the naturally occuring glycine in the 2-position, or other naturally occuring L-amino acids in the naturally occuring amino acid sequence. Other modifications were investigated, but none of these derivatives have met with commercial success despite the concerted efforts of investigators at a number of major pharmaceutical companies, universities and government agencies. None of these derivatives have met with commercial success, and the treatment of moderate to severe acute and chronic pain still requires administration of potent analgesic agents such as codeine, propoxyphene, demerol, morphine and the like.

Thus, a need remains for analgesic agents which provide relief from acute or chronic moderate to severe pain which can not be treated with aspirin, aspirin-like non-steroidal anti-inflammatory agents and acetominophen. The present invention fulfills the long-standing need for safe, effective analgesic agents which can be used in in the treatment of moderate to severe, acute or chronic pain.

D-phenylalanine, DL-phenylalanine, D-leucine and hydrocinnamic acid are known chemicals listed in the Merck Index.

Use of D-phenylalanine has been reported from the Faculty of Medicine, Buenos Aires, Argentina in Therapy of Depression by Phenylalanine" *Arzneim Forsch,* Vol. 25, NR1 (1975), and "Use of D-Phenylalanine in Parkinson's Disease", *Arneim Forsch,* Vol. 26, NR4 (1976). In the report of treatment of depression, DL-phenylalanine was administered in quantities of 50 or 100 mg per day for 15 days, and D-phenylalanine was administered in the amount of 100 mg per day for 15 days.

A commercial drug, sold under the Trademark "Deprenon", is available for treatment of depression by oral ingestion of 3–4 capsules per day. Deprenon's specifications states that each capsule contains:

| | |
|---|---|
| D-Phenylalanine- | 50 mg |
| Mannitol | 90 mg |
| Pervidone | 4 mg |
| Magnesium stearate | 3 mg |

Leucine and phenylalanine are also known to be useful as nutrients.

BRIEF SUMMARY OF THE INVENTION

The present invention provides compositions which are useful in the treatment of pain and/or inflammation comprising a therapeutically effective amount of an analgesic, anti-inflammatory agent selected from the group consisting of D-phenylalanine, DL-phenylalanine, D-leucine, DL-leucine and hydrocinnamic acid, and a synergistically effective amount of a potentiating agent selected from the group consisting of aspirin and a non-steroidal, aspirin-type anti-inflammatory, antipyretic agent.

The first therapeutic agents constitute an entirely new class of analgesics. The most potent of these agents is D-phenylalanine. Hydrocinnamic acid and D-Leucine have also been found to have a significant effect. The combination of D-phenylalanine and D-leucine has proven to result in a potentiation of the analgesic activity of either substance alone. The chronic and non-chronic administration of D-phenylalanine and D-leucine has produced very long-lasting analgesia in mice.

Each of the foregoing substances is available in a powder form and is water soluble. DL-phenylalanine (a mixture of D-phenylalanine and L-phenylalanine) and DL-leucine (a mixture of D-leucine and L-leucine) may be economically used, respectively, as a source of D-phenylalanine and D-leucine whose utility is disclosed herein. The DL-form of those two chemicals is less expensive than the pure D-form of those two amino acids.

The analgesic characteristics of the new class of substances were determined by examining animal reaction to a single treatment, referred to as an "acute" experiment or test, and also to prolonged administration, referred to as a "chronic" experiment or test, to determine if tolerance develops.

The analgesic effect of the new class of substances is enhanced or potentiated by combining the substance with an anti-pyretic, anti-inflammatory analgesic agent such as aspirin or an "aspirin-type" drug. The terms "aspirin-type anti-inflammatory agent" "aspirin-like drug" or "aspirin-type drug", or "an anti-pyretic, anti-inflammatory agent of the aspirin-type" are all synonomous as used herein, and, as used herein means a non-steroidal anti-inflammatory agent ("NAISD") having anti-inflammatory and anti-pyretic activity and which inhibit prostaglandin synthesis.

Such agents include salicyclic acid, sodium salicylate, phenylbutazone, oxyphenbutazone, antipyrine, dipyrone, mefenamic acid, flufenamic acid, ibuprofen, flurbiprofen, fenoprofen, ketoprofen, naproxen, diclofenac, ketoprofen, tolmetin, naproxen, sulindac, phenylbutazone, oxyphenylbutazone, diflusinal, piroxicam, meclofenac and the like. Aspirin and aspirin-type anti-inflammatory agents are known inhibitors of various enzymes, particularly prostaglandin synthetase, enhance or potentiate the action of narcotic analgesics, and such drugs have been used in such combinations of ingredients as: codeine and aspirin and Darvon and aspirin.

Thus, it is an object of the invention disclosed and claimed herein to provide a new combination of analgesic agents in which the analgesic effect of the substances of the combination will be greatly potentiated over the analgesic effect attained when each substance is considered separately, thereby achieving a synergistic effect approaching the analagesic efficacy of morphine.

Potentiation is achieved with sub-therapeutic dosages of aspirin and aspirin-type anti-inflammatory, anti-pyretic agents, thereby reducing the side effects normally experienced with these agents.

Further objects and advantages will become apparent to one skilled in the art as the description of the invention proceeds.

The results of the acute tests, or experiments, are reflected in Tables 1 and 2 set out hereinafter in section "A". The chronic tests and experiments are described in section "B" hereinafter. The results of acute tests, or experiments, using a combination of substances is reflected in Table 3 of section "C" set out hereinafter.

D-phenylalanine in pure form, or as part of DL-phenylalanine has been administered to numerous patients suffering from both acute and chronic pain. Analgesia has been obtained in at least (60%) of the subjects.

A. General Description of Acute Tests of Individual Substances and Effect of Substances Tested The tests herein described were intended to establish the analgesic activity of the analgesic agents and compositions containing those agents, disclosed herein, and to establish at least one safe and practical method of securing in an animal species, such as mammals, a long lasting, or prolonged, analgesic effect.

One test for the ability of the animal to withstand pain is the hot-plate test. It is a traditional pharmacological screening procedure in which drug-treated mice are placed on a hot plate and the analgesic effect of the drug is measured by now soon a mouse jumps off the hot plate. In the specific hot-plate test described herein the temperature of the plate was maintained at 55° C.

Another test for the ability of the animal to withstand pain is the phenylquinone writhing test. Phenylquinone, when injected into mammals such as mice, causes intense pain manifested by stretching, pelvic twisting, and extension of hind legs. An analgesic such as morphine when administered to the mouse, will either abolish or reduce the number of such reactions to phenylquinone, the totality of response being known as writhing.

The practical method of administering the analgesic agents and compositions herein described in mice was by intraperitoneal injection. The dosage injected was 250 mg/kg, the dosage being proportional to the weight of the mouse treated.

The "control" for the hot-plate test was determined by placing an untreated mouse on a metal hot plate maintained at 55° C. The time it takes the untreated or "control" mouse to jump, after being placed on the hot plate, is noted. After being treated by an intraperitoneal injection of drug, the test mouse is again placed on the hot plate, and the laspe of time until the animal jumps is noted. This test of a treated mouse is repeated at various specified times. Specifically, the mouse is tested after a single injection for 2 hours at 30 minute intervals. In the experiments with mice, six to twelve mice were tested with each dose of injected substance. A "highly significant" analgesic effect will be demonstrated by a time lapse, before the mouse jumps, constituting an increase of several-fold (3 or 4) over that of the control.

In the writhing test, the analgesic injected is administered to certain mice approximately one hour before injecting the phenylquinone. Other animals serving as a "control" are injected with saline solution approximately one hour before injecting the phenylquinone. The percent of animals writhing, together with the number of writhes is noted over a period of 10 minutes following injection of the phenylquinone.

The human studies noted herein were carried out on more than 47 subjects experiencing acute and chronic pain which had not been relieved by conventional treatment with drugs or other procedures such as acupuncture, transcutaneous nerve stimulation, or laminectomy. D-phenylalanine plus aspirin, D-phenylalanine alone, or DL-phenylalanine were administered orally and the degree of relief from pain was monitored for a period of several weeks.

The results of all tests were subjected to statistical analysis to determine the degree of significance of results.

EFFECT OF THE SUBSTANCES TESTED

D-phenylalanine and hydrocinnamic acid both exhibited highly significant analgesia by the hot-plate test. This conclusion is supported by the data shown in Table I. With injection of a saline solution, as a control, no significant increase in jump time was observed or noted. With injection of D-phenylalanine or hydrocinnamic acid, a highly significant increase in time lapse before jump was observed.

TABLE 1

| Analgesic Potency As Determined by the Hot Plate Method | |
|---|---|
| Treatment (Injection) | % Increase in Jumping Time |
| Saline | 30%** |
| D-phenylalanine | 300%* |
| L-phenylalanine | 30%** |
| Hydrocinnamic acid | 300%* |

*Highly significant
**Not significant

Specificity of D-phenylalanine as an analgesic agent substance was is determined by comparison of results from its injection with results from injection of L-phenylalanine, a naturally occurring amino acid, whose testing showed minimal, if any, significant analgesic potency. Naloxone exhibits the ability to reverse analgesia produced by D-phenylalanine.

Table 2 shows that injection of D-phenylalanine also significantly decreased the number of test animals showing writhing. Reduction in intensity of writhing is shown by the reduction in number of writhes per minute. Table 2 again shows that injection of L-phenlalanine has relatively little effect.

TABLE 2

| Analgesic Potency of D-Phenylalanine As Determined by the Phenylquinone Writhing Test | | |
|---|---|---|
| Treatment (Injection) | % Writhing | No. of Writhes/ Minute |
| Saline | 90% | 5.4 |
| D-Phenylalanine | 60% | 2.5* |
| L-Phenylalanine | 80% | 4.4** |

*Highly significant
**Not significant

Results using D-leucine in the hot plate and writhing tests are shown in the following Table 3. Just as in the case of D-phenylalanine, analgesia by D-leucine was reversed by naloxone. Results are also shown for the combination of D-phenylalanine and D-leucine in these tests. Such results show the potentiation of action by the combination of these amino acids.

TABLE 3

| Analgesic Potency of D-Leucine and D-Leucine Plus D-Phenylalanine as Determined by the Hot Plate and Phenylquinone Writhing Tests | | |
|---|---|---|
| Treatment (Injection) | Hot Plate % Increase in Jump Time | Writhing Test # of Writhes per minute |
| Saline | — | 5.6 |
| D-leucine, 250 mg/kg | 300* | 3.0* |
| D-leucine, 125 mg/kg + D-phenylalanine, 125 mg/kg | 300* | D-leucine, |
| 250 mg/kg+ D-phenylanine, 250 mg/kg | — | 1.0* |

*Highly significant

B. Chronic Experiments

D-phenylalanine was injected intraperitoneally twice daily for nine (9) days, into mice, in an amount per injection of 250 mg per kg of body weight of the mouse. All animals were tested by the hot-plate test on the ninth day for appearance of analgesia, both before the injection of the phenylalanine as well as afterwards. Two types of controls were also run. One control group of mice was injected with saline solution; the other group was injected with L-phenylalanine. Twenty animals were used for each of these groups.

After administration of the second dose of phenylalanine on the ninth day, the animals that had been injected with D-phenylalanine were injected with naloxone, 15 mg/kg. Naloxone is an antagonist of morphine and the endorphins. The purpose of this latter test was to test for withdrawal symptoms, because with opiate-dependent animals, the amount of injected naloxone will produce severe withdrawal symptoms including diarrhea, large weight loss, and jumping.

The following results were observed in the mice that had been injected with D-phenylalanine for nine (9) days.

(a) Tolerance to the analgesic effects did not develop. In other words, the degree of analgesia in the D-phenylalanine injected mice, as measured by the hot-plate test, on the ninth day was significantly greater than that observed on the first day. If morphine, or other opiate substance, had been administered in a similar fashion, by the ninth day the administration of morphine, in the same amount as administered on the first day would have had very little analgesic effect, the latter result being a reflection of tolerance.

(b) There seems to be a cumulative effect from the repeated injections, over an extended period of time, of D-phenylalanine (i.e., excellent analgesia to the hot plate test was observed in the mice as long as 12 hours after the last dose had been injected.

(c) The control group of mice injected with saline solution or with L-phenylalanine exhibited virtually no analgesia.

The following results were observed, after naloxane injection, in mice that had been injected with D-phenylalanine for nine (9) days:

(d) No sign of addiction was observed from administration of the naloxone test: (i,e, there was no diarrhea, weight loss, jumping, etc.);

(e) Naloxone only abolished the analgesia.

The foregoing results from several tests demonstrate the efficacy of D-phenylalanine and D-leucine as analgesic agents. The substances are effective, do not produce tolerance or dependence, and are extremely safe. Even at very high doses of D-phenylalanine (DPA) given over an extended period of time (1 gm/kg/day for 30 days) no deaths or tissue pathology were observed in any of the experimental animals.

The degree of analgesia obtained with D-phenylalanine is not, initially, as intense as that secured by use of morphine and other narcotic analgesics. It is considered that the analgesia produced by the combination of D-phenylalanine and D-leucine is equivalent to that obtained with fairly large doses of morphine (15 to 20 mg/kg).

C. Potentiation of Analgesia With Anti-inflammatory, Anti-pyretic Agents

It has been discovered that the analgesia produced by D-phenylalanine, D-leucine, DL-phenylalanine, DL-leucine and hydrocinnamic acid can be greatly enhanced, or potentiated, by having a drug having anti-inflammatory and anti-pyretic activity combined therewith. Such anti-inflammatory agents include aspirin and the aspirin-type non-steroidal anti-inflammatory agents (NAISDs). The NAISDs are well known and fall within seven major classes (1) propionic acid derivatives, (2) indole derivatives, (3) fenamates, (4) pyrrolealkanoic acids, (5) pryazolone derivatives, (6) oxicams, and (7) salicylic acids. The NAISDs are similar in mechanism to that of aspirin and are mediated chiefly through inhibition of the biosynthesis of prostaglandins.

The protype of the non-steroidal anti-inflammatory agents is aspirin, and the other anti-inflammatory agents are often referred to as aspirin-type or aspirin-like drugs. (See Goodman and Gilman, *The Pharmacological Basis of Therapeutics*, Sixth Edition, p. 682 (MacMillan Publishing Co., Inc., 1983). These agents include indomethacin(Indocin), diclofenac sodium, ibuprofen (Motrin, Rufen, Advil and Nupren), tolmetin sodium (Tolectin), naproxen (Naprosyn, Anaprox), fenoprofen(Nalfon), sulindac (Clinoril), meclofenamate (Meclomen), mefanimic acid (Ponstel), flurbiprofen, phenylbutazone, oxyphenbutazone, antipyrene, dipryone, flunamic acid, ketoprofen, piroxicam (Feldene), diflusinal (Dolobid), and the like.

Any non-steroidal anti-inflammatory agent (aspirin or any aspirin-type anti-pyretic, anti-inflammatory agent) may be used in the practice of the present invention disclosed and claimed herein.

Significantly, the hot-plate test reflects that injection of, for example aspirin, indomethacin or diclofenac sodium at a dose which failed to provide a significant increase in jumping time of a mouse, when combined with an analegisic agent employed in the practice of this invention, i.e., D-phenylalanine, provided an unusually highly effective analgesia as is reflected in Table 4. Prior to the invention herein, it could not have been predicted that such a combination would produce such an unusual and unexpected effect. In fact, the analgesia obtained by use of the combination of substances approached the analgesia obtained by one of the most potent known analgesics, morphine.

For combination experiments involving D-phenylalanine and representative aspirin-type anti-pyretic, anti-inflammatory agents, the following procedure was used: A series of mice were first administered either indomethacin or diclofenac sodium. At various times, the animals were tested by the hot plate method. After one hour, D-phenylalanine was administered at a dose of 250 mg/kg and the animals were tested for analgesia for another two hours. The results are shown in Table 4. When D-phenylalanine was administered to mice which had previously been treated with an aspirin-type anti-pyretic, anti-inflammatory agent, the effect of the combination was to increase the jumping time 1100 or 1200%, i.e., eleven or twelve-fold. In some instances, the increase was at the maximum equivalent to that of morphine or other narcotic analgesics. It will be recalled from Table 1 above that the same dose of D-phenylalanine caused an increase in jumping time of only 300%, while as shown in Table 4 that of the representative aspirin-type anti-pyretic, anti-inflammatory agents gave essentially non analgesia as measured by the hot plate test. Thus, the results from the combination of the two substances represent a true synergism, or example of drug potentiation.

TABLE 4

| Analgesic Potency of Combinations of D-phenylalanine and Indomethacin or Diclofenac Sodium | |
|---|---|
| Treatment | % Increase in Jumping Time |
| D-phenylalanine, 250 mg/kg | 300 |
| Indomethacin, 20 mg/kg | 0 |
| Indomethacin, 20 mg/kg followed by D-phenylalanine, 250 mg/kg | 1100* |
| Diclofenac sodium, 40 mg/kg | 33 |
| Diclofenac sodium, 40 mg/kg followed by D-phenylalanine, 250 mg/kg | 1200* |

*Highly significant potentiation

Preliminary experiments in treatment of pain in human subjects using D-phenylalanine plus aspirin, or DL-phenylalanine, administered orally, shows that the efficacy of these substances as analgesics in man has been confirmed. As shown in Table 5 which lists representative results, long lasting pain relief can be achieved with any of the above mentioned chemicals, including combinations of D-phenylalanine, DL-phenylalanine, D-leucine, DL-leucine and hydrocinnamic acid aspirin-type anti-pyretic, anti-inflammatory agents given for three or four days. No side effects, tolerance or signs of addiction were observed in any patient.

Preliminary success in experiments in treatment of pain in human subjects was also achieved using D-leucine.

TABLE 5

| D-Phenylalanine (DPA) Analgesia In Humans | | | | |
|---|---|---|---|---|
| Condition | Duration | Prior Treatmt. | Time on DPA | Result |
| Whiplash | 2 years | Empirin, Valium | 3 days | Complete relief, 1 month |
| Osteo-arthritis, fingers, thumbs of both hands | 5 years | Empirin + aspirin | Maintained | Excellent relief, relief, joint stiffness reduced |
| Rheumatoid arthritis left knee, Osteo-arthritis of hands | Several years | Empirin + codeine | 1 week | Considerable relief |
| Low back pain, neck pain | Several years | Spinal fusion, percutaneous nerve stimulation | 3 days | Much less pain |
| Low back pain | Several years | 90 acupunctures | 3 days | Back pain gone, walked one mile |
| Low back pain | Several years | Laminectomies, Depomedrol, percutaneous nerve stimulation | 3 days | Good to excellent relief |
| Fibrositis of muscle | * | Empirin | 2 days | Pain gone, recurred after 2 days |
| Migraine | Several years | * | 2 days | Good relief, may prevent recurrence |
| Cervical osteo-arthritis plus post-operative pain | * | * | 2 days | Very little pain |
| Severe lower back pain | Several years (Intermittent) | Empirin Valium | 3 days | Excellent relief |

*Means information not available

In the treatment of pain in human subjects, reported in Table 5, the dosage of D-phenylalanine administered was in the range of 800–1,000 mg per day, administered in 4 equal dosages of 200–250 mg per dose. These amounts had been selected conservatively. When administration was with aspirin, 300 mg of aspirin was added to the D-phenylalanine. When DL-phenylalanine was administered, the dosages were doubled to 400–500 mg per dose, since the D-phenylalanine component of the DL-phenylalanine was 50%. In all cases where the DL form of phenylalanine or leucine is employed, the dosage of the D-form is doubled.

The preferred dosage range for D-phenylalanine is 400–3,000 mg per day, preferably taken in four divided dosages of from 100–750 mg per dose. When the preferred dosage range is administered with aspirin, the aspirin component will range from 125 to 950 mg per dosage. Three hundred mg per dose is preferred.

Aspirin and the aspirin-type anti-pyretic, anti-inflammatory agents are employed in amounts of from one-forth their normal therapeutic dose, to and including their therapeutic dosages, depending upon patient response. Generally speaking, potentiation is achieved with sub-therapeutic dosages, however, in cases where an immediate response is not achieved, the dosage of aspirin, or an aspirin-type drug may be increased in combination with, for example DPA, until analgesia is obtained, and then lowered.

The therapeutically effective amounts or dosages of the aspirin-type drugs useful in the practice of this invention are set forth, in for example, the Physician's Desk Reference and may be used as a pharmaceutically acceptable salt.

It has also been determined by experimentation with animals that D-phenylalanine itself exhibits anti-inflammatory activity. The anti-inflammatory activity of D-phenylalanine was determined as follows:

RAT PAW CARRAGEENAN TEST FOR ANTI-INFLAMMATORY ACTION OF D-PHENYLALANINE

The rat paw carageenan test is a standard test for determining whether a drug can act as an anti-inflammatory agent in man. Carageenan is a highly irritating substance and cases swelling of tissues when injected. An anti inflammatory agent is one which can counteract such swelling. A convenient tissue for accurately measuring the degree of swelling is the hind paw of the rat which swells up greatly when the carageenan is injected. The degree of swelling is easily measured by immersing the paw in water and noting the degree of fluid displacement. In the experiments carried out, DPA was administered either orally or intraperitoneally 2–3 hours before the carageenan. The effect of DPA was compared with that of control paws of animals administered saline instead of DPA.

TABLE 6

| Activity of D-Phenyalanine in Rat Paw Carageenan Test | | | |
|---|---|---|---|
| DPA (mg/kg) | Route | Time Before Carageenan | % Inhibition Swelling |
| 1000 | i.p. | 120 | −71 |
| 500 | i.p. | 120 | −59 |
| 250 | i.p. | 120 | −61 |
| 125 | i.p. | 120 | −61 |
| 1000 | oral | 180 | −30 |
| 500 | oral | 180 | −42 |
| 250 | oral | 180 | −35 |
| 125 | oral | 180 | −38 |

In view of the results obtained by experimentation with D-phenylalanine, D-leucine, DL-phenylalanine, DL-leucine and hydrocinnamic acid, and mixtures thereof, alone, and in combination with aspirin and other aspirin-type or aspirin-like non-steroidal anti-pyretic, anti-inflammatory agents, the latter yielding synergistic effect, the present invention provides methods and compositions for treating pain and inflammation in mammals including humans. The combination therapy is particularly suited to patients who initially do not respond to treatment with D-phenylalanine, D-leucine, DL-phenylalanine, DL-leucine or hydrocinnamic alone.

The compositions of the present invention are preferably solid oral unit dosage forms comprising a therapeutically effective amount of an analgesic agent selected from the group consisting of D-phenylalanine, DL-phenylalanine, D-leucine, DL-leucine and hydrocinnamic acid, in combination with each other or aspirin or an aspirin-type anti-pyretic, anti-inflammatory agent. The compositions may additionally comprise binders, fillers, lubricants, colorants, and the like, and are prepared by methods well known in the art.

The term "pharmaceutically acceptable salt", as used herein refers to the physiologically acceptable, nontoxic salts of the non-steroidal anti-inflammatory agents employed in the practice of this invention.

The invention claimed is:

1. An analgesic composition comprising: a therapeutically effective amount of an analgesic agent selected from the group consisting of D-phenylalanine, DL-phenylalanine, D-leucine and DL-leucine and a synergistically effective amount of aspirin.

2. The composition of claim 1 wherein said analgesic agent is D-phenylalanine.

3. The composition of claim 1 wherein said D-phenylalanine is present in an amount of from 100 to 750 mg per unit dosage.

4. The composition of claim 1 wherein aspirin is present in an amount of 300 mg per unit dosage.

5. The composition of claim 1 wherein aspirin is present in an amount of from 125 to 950 mg.

6. The composition of claim 1 wherein said analgesic agent is DL-phenylalanine.

7. The composition of claim 1 wherein said analgesic agent is D-leucine.

8. The composition of claim 1 wherein said analgesic agent is DL-leucine.

9. An anti-inflammatory composition in solid oral unit dosage form comprising: a therapeutically effective amount of a compound selected from the group consisting of D-phenylalanine, DL-phenylalanine, D-leucine, and DL-leucine and a synergistically effective amount of aspirin.

10. The composition of claim 9 wherein said compound is D-phenylalanine.

11. The composition of claim 9 wherein said D-phenylalanine is present in an amount of from 100 to 750 mg per unit dosage.

12. The composition of claim 9 wherein aspirin is present in an amount of from 125 to 950 mg per unit dosage.

13. The composition of claim 12 wherein aspirin is present in an amount of 300 mg per unit dosage.

14. The composition of claim 9 wherein said compound is D-phenylalanine.

15. The composition of claim 9 wherein said compound is DL-leucine.

16. The composition of claim 9 wherein said compound is DL-phenylalanine.

17. A pharmaceutical composition in oral unit dosage form comprising from 100 to 750 mg of D-phenylalanine and a synergistically effective amount of aspirin.

18. A pharmaceutical composition in oral unit dosage form comprising from 200 to 1500 mg of DL-phenylalanine and a synergistically effective amount of aspirin.

* * * * *